United States Patent [19]

Babler et al.

[11] Patent Number: 4,801,535
[45] Date of Patent: Jan. 31, 1989

[54] METHOD FOR DETECTION OF PERIODONTAL DISEASE

[75] Inventors: Scott D. Babler, Park Ridge; Peter Baram, Chicago; Paul H. Rudolph, Glenwood; Frank J. Waxman, Bolingbrook, all of Ill.

[73] Assignee: Xytronyx, Inc., Chicago, Ill.

[21] Appl. No.: 840,890

[22] Filed: Mar. 18, 1986

[51] Int. Cl.$^4$ .............................................. C12Q 1/52
[52] U.S. Cl. .................................... 435/16; 435/24; 435/184; 435/810
[58] Field of Search .................... 435/15, 16, 24, 184, 435/810

[56] References Cited

U.S. PATENT DOCUMENTS

| | | |
|---|---|---|
| 3,691,018 | 9/1972 | McNamara . |
| 3,723,064 | 3/1973 | Liotta ..................................... 436/66 |
| 3,814,669 | 6/1974 | Goldenberg ........................... 435/16 |
| 3,875,014 | 4/1975 | Forgione . |
| 3,899,397 | 8/1975 | Morin et al. . |
| 4,042,335 | 8/1977 | Clément ................................. 435/14 |
| 4,059,407 | 11/1977 | Hochstrasser . |
| 4,471,055 | 9/1984 | Opp . |
| 4,654,310 | 3/1987 | Ly ..................................... 435/805 |

FOREIGN PATENT DOCUMENTS 0151536  8/1985  European Pat. Off. .

OTHER PUBLICATIONS

Morin et al., Cun. Chem. 19(7) 776-778 (1973).
Bergmeyer, Methods of Enzymatic Analysis, Third Edition, vol. 1, verlag chemie, GmbH, Weinheim, 1983, pp. 27, 28, 109-113, 126-127.
Chambers, et al., Chemical Abstracts, vol. 101 (Nov. 19, 1984) #189179h.
Rej, "Measurement of Aminotransferases: Part 1. Aspartate Aminotransferase", CRC Critical Reviews in Clinical Laboratory Sciences, vol. 21, No. 2, pp. 98-186 (1984).

Primary Examiner—Christine M. Nucker
Attorney, Agent, or Firm—Marshall, O'Tolle, Gerstein, Murray & Bicknell

[57] ABSTRACT

Disclosed are improvements in methods for determining the presence of suprathreshold amounts of aspartate aminotransferase in an oral fluid sample by (1) incubation of aspartate aminotransferase substrate materials in a first reaction mixture with the sample to form a first reaction product and (2) detection of reaction product therein by incubation with an indicator substance in a second reaction mixture wherein a second colored reaction product is formed. The improvement comprises (a) utilizing a diazonium dyestuff as the indicator substance in the second reaction and (b) modifying reaction conditions within the first and second reaction mixtures such that no visually detectable colored reaction product will be formed in the second reaction mixture by subthreshold level of aspartate aminotransferase but wherein a visually detectable color reaction product will be formed in the reaction mixture when a selected suprathreshold concentration of aspartate aminotransferase is present in the first reaction mixture.

15 Claims, No Drawings

METHOD FOR DETECTION OF PERIODONTAL DISEASE

BACKGROUND OF THE INVENTION

The invention pertains to methods of determining the presence of periodontal disease in mammals, and more particularly to improved methods of determining active periodontal disease by assaying for the presence of suprathreshold levels of the enzyme aspartate aminotransferase in oral fluid samples.

Periodontal diseases are inflammatory diseases of microbial etiology affecting the supporting tissues of the teeth. These diseases, which affect over 70% of the adult population, are the leading causes of tooth loss in people over 35 years of age. Costs associated with periodontal disease, including cost of treatment and the economic cost due to loss of productivity, is extremely high. It was estimated in 1976 that the cost of effective management of all those suffering from periodontal disease (more than 100 million people) would be many times the 1.5 billion dollars spent at that time [see "Evaluation of NIDR Periodontal Disease Research Activity—Report of the Ad Hoc Scientific Evaluation Panel", National Institutes of Dental Research, Washington, D.C. (April 1976)].

The term "periodontal disease" encompasses two major subclasses of disease, gingivitis and periodontitis. "Gingivitis" is characterized by inflammation of the gums in the absence of bone and attachment loss. See, Loe, H. and P. Silness, Acta Odont. Scand. 21:533 (1963). "Periodontitis" is generally accepted to be an advanced stage of gingivitis, further characterized by formation of periodontal pockets between the gum tissue and tooth, followed by loss of bone from the tooth and weakening of tooth attachment, eventually leading to tooth loss. See, Ramfjord, S., J. Periodontal. 38:602 (1967). Periodontitis may be further classified, e.g., juvenile periodontitis, local periodontitis, acute necrotizing periodontitis, chronic inflammatory periodontitis (CIPD). CIPD is the most common form of periodontitis among American adults and is characterized by loss of attachment of periodontal ligament to cementum, apical migration of junctional epithelium, and loss of alveolar bone. Both gingivitis and periodontitis are characterized by accumulation of crevicular fluid (a transudate of serum) at the junction of the teeth and gums.

Although periodontal disease is one of the most prevalent bacterial diseases in the civilized world, its diagnosis has been based, until recently, primarily upon subjective observational indices sch as those of Loe and Silness, supra, for gingivitis and Ramfjord, supra, for periodontitis. These indices are based on criteria such as bleeding on gentle probing, pocket depth, attachment loss and radiographic evidence of bone loss. Unfortunately, these clinical indicators, with the exception of bleeding on probing (bleeding of gum tissue due to probing of the gum line or pocket with a hard instrument, e.g. probe or curet), are generally acknowledged to be reflective of prior damage resulting from past disease as opposed to active periodontal disease. Further, even the diagnostic value of bleeding on probing has been questioned. See, Haffajee, Socransky and Goodson, J. Perio. 10:257–265 (1963). Characteristics additionally hindering diagnosis of the disease arise from the fact that in its early stages it may be asymptomatic and that it is frequently episodic, with a cyclical pattern of destructive activity interspersed with periods of latency or spontaneous partial regression.

Recently, several novel methods for the diagnosis of periodontal disease have been developed. One method takes advantage of the fact that gingivitis and periodontitis are characterized by the accumulation of crevicular fluid at the junction of the teeth and gums. Measurement of a large volume of crevicular fluid between the teeth and gums can indicate the presence of periodontal disease. An instrument known as the Periotron (Harco Electronics Ltd.; Winnipeg, Canada) is used to galvanometrically measure the volume of crevicular fluid absorbed by small strips of porous material known as Periopaper (Harco; Tustin, Calif.) which are inserted into the crevicular space between the tooth and gum.

McNamara, U.S. Pat. No. 3,691,018 discloses a diagnostic method for the early detection of incipient disease wherein crevicular fluid is tested for the presence of $\beta$-D-galactosidase. The patent discloses that a strip formed from a nylon Millipore filter having a pore size of one micron may be used to collect crevicular fluid. The fluid is then tested for the presence of $\beta$-D-galactosidase at two different pH's (5.0 and 7.5) one indicative of mammalian produced enzyme and the other indicative of bacterial produced enzyme. The porous strips are incubated for approximately 2 hours at 37° C. with suitable substrates in buffer solution at pH 5 and pH 7.5. The strips are then removed and post-coupled with a diazonium salt for one minute to produce a color reaction. The intensity of color reaction for the sample at each pH is judged according to a standard of (1) no color; (2) slight intensity; (3) moderate intensity or (4) deep intensity. Color intensities of samples incubated at each of the two pHs are determined and compared to a master table in order to determine the presence and severity of periodontal disease.

Recently it has been disclosed, however, that the presence of elevated levels of the enzyme aspartate aminotransferase (AST) in crevicular fluid is highly correlative of the presence of active periodontal disease. Chambers, EPO patent application Publication No. 151,536 published Aug. 14, 1985. The presence of elevated levels of this enzyme in crevicular fluid is also disclosed to be predictive of a high probability of progressive, as opposed to non-progressive, periodontal disease and corresponding tissue damage. Increased levels of blood serum AST have previously been correlated with a wide variety of other conditions including acute myocardial infarction, pulmonary embolism, acute pancreatitis, viral and toxic hepatitis, and acute cirrhosis.

The enzyme aspartate aminotransferase [EC 2.6.1.1; L-aspartate:2-oxoglutarate aminotransferase] (previously known as glutamic aspartic transaminase, glutamic aspartic aminotransferase, glutamic aspartic aminopherase, glutamic oxaloacetic transaminase, GOT, G. O. T., or GO-T) (hereinafter referred to as AST) catalyzes the reaction:

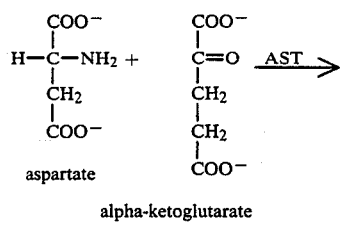

aspartate    alpha-ketoglutarate

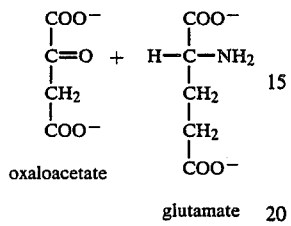

oxaloacetate    glutamate

Pyridoxal phosphate is required as a prosthetic group. The enzyme also catalyzes other reactions (e.g., betasulphinyl pyruvate to L-cysteinesulphonate and betasulphonyl pyruvate to L-cysteate) but at a much slower rate.

AST is found in both the mitochondria and cytoplasm of eukaryotic cells. Both forms have a molecular weight of about 90,000 daltons and consist of 2 approximately equal size subunits, but differ in their physical and chemical characteristics and amino acid composition. AST is involved in a variety of catabolic and anabolic pathways for amino acids. See Lehninger, A. L., *Biochemistry*, 2nd ed. (Worth Publishers, New York, 1975).

According to the method of Chambers, crevicular fluid is collected from the interface of the gum and tooth by means such as a microsyringe, capillary tube or absorbant strip. The volume of material is measured and the presence of AST in the collected sample of crevicular fluid is determined by either colorimetric or immunological assay.

A wide variety of colorimetric assays are known for the detection of AST in serum. These assays actually analyze for the presence of oxaloacetate formed from the AST catalyzed reaction of aspartate and alpha-ketoglutarate. In one procedure, the production of oxaloacetate by Reaction I, supra, is coupled with the formation of a 2,4-dinitrophenyl-hydrazone-derivative which has a reddish-brown color and absorbs light at 520 nm:

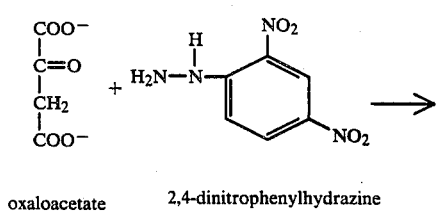

oxaloacetate    2,4-dinitrophenylhydrazine    (II)

-continued

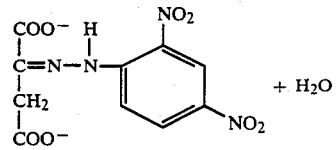

oxaloacetate-2,4-dinitrophenylhydrazone

In these procedures, the serum sample is incubated with excess amounts of L-aspartic acid and alphaoxoglutaric acid and excess 2,4-dinitrophenylhydrazone is then added. The reaction mixture is then further incubated to allow for conversion of any oxalacetate to its 2,4-dinitrophenylhydrazone derivative the color of which is brought out by addition of excess alkali. Chambers, supra, discloses use of this technique for the detection of AST present in crevicular fluid.

There are several disadvantages to procedures utilizing 2,4-dinitrophenylhydrazone, however. Incubation times are long and oxaloacetate accumulates over the course of the enzyme reaction resulting in inhibition of both isoenzymes. Further, mitochondrial AST is more sensitive to product inhibition and tends to be underestimated by this procedure.

In an alternative procedure known for use in detection of serum AST and disclosed by Chambers, supra, for detection of AST in crevicular fluid, oxaloacetate produced by reaction I is converted to pyruvate which is subsequently converted to the pyruvate-2,4-dinitrophenylhydrazone derivative. The excess aniline citrate is added after incubation of the sample with the substrate and before addition of the 2,4-dinitrophenylhydrazone reagent. After addition of the 2,4-dinitrohydrazone, the reaction mixture is incubated to allow for conversion of the pyruvate to its dinitrophenylhydrazone derivative which is brought out by the addition of excess alkali.

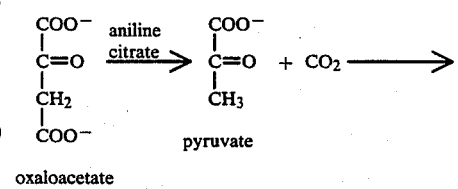

oxaloacetate    pyruvate    (III)

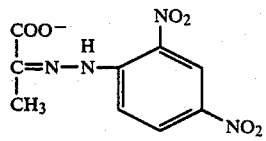

pyruvate-2,4-dinitrophenylhydrazone

Examples of commercially available AST assays using this procedure are A-gent ™ Aspartate Aminotransferase Assay (Abbott Cat. No. ABA-50, ABA-100, Abbott-VP, Abbott Laboratories, Chicago, Ill.), and Worthington Statzyme ® GOT (Worthington Cat. No. CGOT, Worthington Diagnostic Systems, Inc., Freehold, N.J.).

Also known for the detection of AST are methods utilizing azozene dyes for reaction with oxaloacetate. These methods are significantly more rapid than those utilizing 2,4-dinitrophenyl hydrazone, do not cause product inhibition of AST and avoid use of alkali in developing the color reaction. Forgione, U.S. Pat. No. 3,875,014 discloses test indicators for the determination of AST concentrations in sera utilizing the pair of reactions

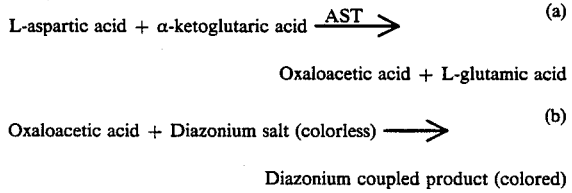

The test indicator of Forgione, comprises a pair of bibulous materials, adhered to each other with an adhesive which is selectively permeable to oxaloacetic acid, the first of which comprises the substrates L-aspartic acid and α-ketoglutaric acid. The second comprises a dried diazonium salt. The indicator is contacted with sera which, if it contains AST, catalyzes the reaction of the substrates to form oxaloacetic acid. Oxaloacetic acid then diffuses to the second strip and activates a color reaction with a diazonium salt.

Methods and various materials for the detection of AST utilizing diazonium salts are disclosed in Rej, "Measurement of Aminotransferases: Part 1. Aspartate Aminotransferase", CRC Critical Reviews in Clinical Laboratory Sciences, Vol. 21, No. 2, pp. 98–186 (1984). This reference discloses suitable diazonium salts including, Fast Violet B, {4-amino-2.5-diethoxy benzanilide (6-benzamido-4-methoxy-5-toluidine) diazonium chloride}; Fast Red PDC/Ponceau L, {N'-butyl-4-methoxymetanilamide diazonium salt}; Fast Red KL, {2-amino-4-methoxybenzamide diazonium salt}; Fast Scarlet GG, 2.5-dichloroaniline diazonium salt]; Fast Red RC, {5-chloro-2-methoxyaniline-1-diazonium chloride}; Fast Blue BB, {4-amino-2.5-diethoxybenzanilide diazonium chloride.}; Fast Blue B, {3.3'-dimethoxydiphenyl-4,4'-tetrazonium chloride} and Fast Blue RR, {4-amino-2.5-dimethoxybenzanilidine diazonium chloride}. Use of diazonium salts for detection of AST as disclosed in Forgione and Rej require either the subjective evaluation of color intensities as compared against a color chart or automated procedures which are only semi-quantitive and suffer from difficulties in calibration.

Because of the problems associated with techniques utilizing 2,4-dinitrohydrazone or diazonium dyes, a preferred alternative procedure is known wherein oxaloacetate produced by AST catalyzed reaction of L-aspartate and alpha-ketoglutarate is converted to malate in a second reaction by malate dehydrogenase with the cofactor nicotine adenine dinucleotide (NAD), in the presence of its reduced form, nicotine adenine dinucleotide (NADH). See, Hochstrasser, U.S. Pat. No. 4,059,407. NADH absorbs ultraviolet light at 340 nm, thus the rate of conversion of oxaloacetate to malate can be followed by monitoring the rate of disappearance of NADH at 340 nm. While the NADH system has the disadvantage of requiring a spectrophotometer (because NADH absorbs light in the ultraviolet spectrum) it has advantages of reproducibility and of quantitativeness as oxaloacetate is removed from the reaction mixture during the course of reaction so as to prevent product inhibition. Because of its numerous advantages, the system is considered the most durable and is currently the basis for national and international efforts for standardization of AST measurements. Rej, supra. The diazonium salt AST detection systems have largely been superseded by the NADH system in all areas with the exception of specialized (nonquantitative) electrophoretic applications. Rej, supra, pp. 139–141.

Desired by the art are techniques whereby the presence of a compound in excess of a predetermined concentration may be detected by a simple yes-no test not requiring a color chart. Opp, U.S. Pat. No. 4,471,055 discloses a process and a kit for the detection of aldehyde concentrations in a sample in excess of a predetermined concentration. Two reaction systems are employed. The first reaction system acts in transforming quantitatively to a first reaction product the amount of aldehyde equal to the predetermined concentration. The second reaction system then acts to transform any remaining aldehyde to a second reaction product which is visibly detectable.

Hochstrasser, supra, discloses disposable chemical indicators for the measurement of concentrations of a wide variety of materials in biological fluids including ketones, proteins and AST. The indicator registers the concentration of substance detected with multiple indicia which read either "on" or "off" at specific threshold values and thus eliminate the need for subjective judgment of color intensity and the need for color charts and the like. Reagents are used which give a visual indication when exposed to specific concentrations of the substance to be tested. The patent discloses reagent systems which comprise a fixed amount of a titrant which reacts with one of the products in a reduction involving the material being analyzed and proceeding to completion with the formation of one or more products, one of which reacts quantitatively with the titrant, and is thus not permitted to accumulate (and produce a color signal) until all of the titrant is consumed at which time the accumulation of the product becomes visible to the eye or to a spectrophotometric device.

Hochstrasser, utilizes the NADH/malic acid, reaction system for the detection of AST with indicator systems disclosed as follows:

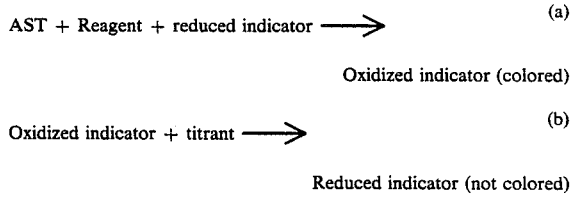

Aspartic acid, alpha-ketoglutaric acid, malic acid dehydrogenase and NADH are identified by Hochstrasser as "reagents". Suitable indicators are disclosed to include o-dianisidine, p-toluidine, 2.2'-azino-di-(3-ethyl-benzothiazoline-o-sulphonic acid) (ABTS), p-diphenylamine sulfonic acid, o-tolidine, natural red (cert.), janus green B (cert.), 2,6-dibromoindophenol sodium salt (prac.) and NN-dimethyl indoaniline (pract.). Suitable titrants are disclosed to include reductants such as gentisic acid, ascorbic acid, hydroquinone, pyrogallol, hydroxylamine, sodium nitrite, sodium bisulfite, sodium thiosulfate, cysteine, hydrazine, ferrous ion and complexes thereof and cuprous ion and complexes thereof.

Despite the existence in the art of tests for the detection of periodontal disease, there remains a need in the art for improved tests with are rapid, inexpensive and sufficiently simple that they may be used with a minimum of difficulty in a dentist's office or by a layperson in the home. Such tests should be eye readable, rather than spectrophotometric, and provide an objective indication of the existence of the disease state with minimal requirements for subjective judgment as to color intensity. Further such tests should avoid the need for adding caustic chemicals such as sodium hydroxide.

BRIEF SUMMARY

The present invention provides an improvement in methods for detection of the presence of aspartate aminotransferase in an oral fluid sample which may be saliva or crevicular fluid through the incubation of substrates in a first enzyme reaction mixture with the sample to form a reaction product which is itself detected by reaction with an indicator substance in a second color reaction. More particularly, the invention relates to methods for the detection of the presence of active periodontal disease in mammals through the detection of suprathreshold concentrations of aspartate aminotransferase in oral fluid samples. The invention provides a new rapid and inexpensive method for the detection of periodontal disease. The test is eye readable rather than spectrophotometric and provides an objective qualitative indication of the presence or absence of periodontal disease which does not indicate false positive results due to the presence of background levels of AST and requires a minimum of subjective judgment as to color intensity. The test provides a distinct and unambiguous color signal upon the presence in oral fluid of a threshold amount of AST indicative of the presence of periodontal disease. The method comprises (a) absorbing a limited volume of oral fluid on a solid support; (b) forming a first reaction mixture through incubating the solid support in the presence of a substrate under conditions wherein no detectable quantity of enzyme catalyzed reaction product will be formed in the reaction mixture by a subthreshold quantity of AST but wherein a detectable quantity of enzyme-catalyzed reaction product will be formed in the reaction mixture in the presence of a suprathreshold concentration of AST; and (c) incubating the reaction mixture of (b) in the presence of a diazonium dyestuff capable of eliciting a color change when contacted with a detectable quantity of enzyme-catalyzed reaction product of (b).

DETAILED DESCRIPTION

According to the practice of the invention, oral fluid is sampled from the mouth. The fluid may be saliva or preferably crevicular fluid. Crevicular fluid may be sampled from the intracrevicular space between the tooth and gum. Saliva may be sampled from the surfaces of the teeth and mouth tissue. A quantity of the oral fluid is then placed on a solid support which may be placed into a sample chamber and incubated with a substrate under specified conditions. These conditions are such that where levels of AST present in the sample are below a predetermined threshold no visually detectable quantity of enzyme-catalyzed substrate reaction product will be formed. Where levels of AST present in the sample exceed the predetermined threshold, however, a detectable quantity of enzyme-catalyzed substrate reaction product will be formed. The reaction mixture is then preferably incubated in the presence of a dye stuff capable of eliciting a color change when contacted with detectable quantities of the enzyme-catalyzed reaction product such that the production of a color signal is indicative of the presence of a suprathreshold quantity of AST and conversely, the absence of such a signal is indicative of subthreshold levels of AST. The reaction conditions may be adjusted in order to raise or lower the detection threshold according to levels of AST considered to be clinically significant.

Oral fluid samples may be saliva or crevicular fluid. Samples of saliva may be collected from the mouth by a variety of means such as adsorption onto porous solid support materials such as filter paper. Crevicular fluid may be collected from the interface of the gum and tooth by a variety of means according to the present invention including a microsyringe with a fine (preferably blunt) needle or a capillary tube (preferably calibrated). Samples may also be obtained by means of pledgets, cotton swabs or filamentous material such as dental floss. Preferably, such fluid is sampled by means of absorbant strips of paper or fabric and most preferably by endodontic paper points known as Periopaper (Harco; Tustin, Calif.). The sample is collected by direct contact of the sampling means with crevicular fluid at the interface of the tooth and gum. The amount of sample is determined by calibration of the collection means, or alternatively by subsequent measurement. The amount of fluid on a filter paper strip may be determined by means of a galvanometer such as a Periotron. Maximum amounts collected on such filter paper strips may also be roughly limited by appropriate sizing of the absorptive portions of the strips. Minor variations in volumes of fluids absorbed (e.g., 10% variations) are not expected to materially alter the accuracy of the testing method. It should be noted, however, that while results recorded for samples of crevicular fluid should reflect the condition of the gum at the position specifically tested, results recorded for samples of saliva will tend to reflect the average condition of gum in the multitooth area from which the sample is obtained.

The oral fluid sample, obtained by whatever means, is then absorbed onto a porous solid support. Porous solid support materials useful with the invention include fibrous materials such as paper and woven and nonwoven fabrics. As to their chemical nature, they may be (a) natural polymeric carbohydrates and their synthetically modified, cross-linked or substituted derivatives including cellulose and cellulose esters; (b) natural polymers including proteins and their derivatives; (c) natural hydrocarbon polymers such as latexes and rubbers; (d) synthetic polymers which can be prepared with suitably porous structures; (e) inorganic materials which can be prepared in suitably porous form or which can be used as fillers in one of the above polymeric materials or (f) mixtures or copolymers of the above classes. A preferred material is endodontic filter paper manufactured from cellulose fibers available commercially as Periopaper (Harco; Tustin, Calif.). This material is suitable for use both as a collection means and as a sample support.

Substrate materials suitable according to the invention include those materials which are subject to quantitative conversion by means of an AST catalyzed reaction to a reaction product which may be detected by reaction with a dyestuff. Such materials include L-aspartate, L-glutamate, oxalacetate, alpha-ketoglutarate, as well as alanine, alanosine, aminoadipate, $\beta$- hydroxyaspartate, cysteine, cysteine sulfonate, 5-hydroxytryptophan, hydroxyphenylpyruvate, kynurenine, DOPA, tyrosine, phenylalanine, phenylpyruvate, pyruvate and tryptophan. Reaction products of AST catalyzed conversion of these substrates may be converted by further chemical reaction to products which themselves are capable of reacting with a dyestuff to produce a detectable color signal. Substrate solutions useful with the present invention can comprise suitable buffer materials at a variety of pHs including phosphates, borates and barbitols but preferably including Tris-HCl at a pH of 7.0 to 8.0. Stabilizers such as bovine serum albumin (BSA) may also be included with the composition. A preferred substrate solution comprises 5 mM sodium alpha-ketoglutarate and 20 mM sodium L-aspartate in a 0.M Tris-HCl buffer solution pH 8.0 (pH 7.96 after addition of substrates to the buffer).

Dyestuffs suitable according to the invention include those dyestuffs capable of reacting with the reaction products formed by the AST catalyzed conversion of the substrates. Preferred materials include diazonium salts such as Fast Violet B, Fast Red PDC/Ponceau L, Fast Red KL, Fast Scarlet GG, Fast Red RC, Fast Blue B, and Fast Blue RR. Most preferred is the diazonium salt Fast Blue BB. A suitable coupling material may be prepared from this material by mixing from about 1–20 mg and preferably about 2–10 mg of Fast Blue BB salt in 1 ml of deionized water.

In the practice of the invention, a first reaction mixture is formed by incubating the solid support upon which oral fluid sample has been adsorbed in the presence of a substrate. In order to prevent drying of the solid support, it has often been found advantageous to add a small amount of buffer solution and a stabilizer/carrier protein such as serum albumin to the well or tube in which the solid support will be incubated. The solid support upon which the fluid sample has been absorbed may then be placed in the well or tube followed by addition of the substrate materials. The fluid sample and substrate are then incubated under specified conditions. These conditions are such that no detectable quantity of enzyme catalyzed reaction product will be formed in the presence of a subthreshold amount of AST in the fluid sample. The conditions, however, are such that the presence of a suprathreshold quantity of AST will result in the formation of a detectable quantity of enzyme-catalyzed reaction product which is capable of eliciting a color change in the presence of a suitable dyestuff. The quantity of AST present determines the rate at which the particular reaction proceeds. Thus in reaction systems where AST participates as a catalyst it is necessary to impose a suitable time course limitation on the AST catalyzed reaction of the substrate and thereby determine the extent of catalyzed reaction at a particular time. The AST catalyzed reaction at the end of this time course may be discontinued by introduction of an enzyme inhibitor, changing the pH of the reaction solution to inactivate the reaction, addition of a diazonium dye salt which serves to inhibit the AST enzyme reaction or other methods. The diazonium dye salt, Fast Blue BB, when added at concentrations of about 2 mg per ml of AST/substrate solution, has been found to almost completely inhibit the enzyme reaction where AST is present in concentrations less than about 4000 sigma units per ml while the dye salt is capable of less complete inhibition at AST concentrations ranging to 10000 units per ml and higher. The methods according to the present invention allow a significant degree of flexibility with respect to time such that the exact time at which an assay is read or at which the reaction is inhibited is not critical to the accuracy of the assay.

The rate of the first enzyme reaction can be modified by the incorporation of enzyme inhibitors, by variation in substrate concentration, by alteration of reaction pH, by alteration of buffer concentration, by variation of temperature or by other methods as would be apparent to one of ordinary skill in the art. The rate of the second color reaction can be modified by variation in buffer concentration and pH as well as by variation in dyestuff concentration.

Appropriate reaction conditions may be easily determined for par icular substrates and diazonium dyestuffs according to well known techniques in the art. The following examples are illustrative of various aspects of the invention and are not to be construed as limiting.

Example 1 describes a system for the detection of AST utilizing aspartate and alpha-ketoglutarate as substrates and Fast Blue BB salt as a dyestuff. Example 2 describes systems in which assays are conducted at various buffer molarities, enzyme reaction times and color reaction times. Example 3 describes systems in which assays are conducted at various buffer pH values and buffer is added to the dyestuff mixture. Example 4 describes systems in which assays are conducted with various concentrations of substrate. Example 5 describes systems in which assays are conducted with various concentrations of Fast Blue BB dyestuff. Example 6 describes systems in which assays are conducted utilizing Fast Blue BB salt dyestuff mixed with HCl at various concentrations. Examples 7 and 8 describe systems in which assays are conducted with various concentrations of AST reaction inhibitor.

EXAMPLE 1

In this example, an assay of the enzyme AST in crevicular fluid is performed using reagents supplied in kit form. Approximately 1 μl of crevicular fluid is collected on a Periopaper strip which is placed into a reaction container with a volume of approximately 100 μl.

Substrate solution is prepared by mixing a dry powder consisting of 31.0 mg of L-sodium aspartate and 8.4 mg of sodium alpha-ketoglutarate with 10 ml of 0.1M Tris-HCl buffer solution (pH 8.0). These components are mixed by vigorous shaking for approximately 2 minutes at which time the solid components are dissolved in the buffer solution. Fifty microliters (approximately 1 drop) of substrate solution is then placed in the reaction container to cover the Periopaper strip. The substrate solution and crevicular fluid are then allowed to incubate for 15 minutes at room temperature.

A coupling solution comprising Fast Blue BB diazonium salt is prepared immediately prior to use by dissolving 10mg of Fast Blue BB salt in the form of a powder into 1 ml of distilled water. After the 15 minute initial incubation, 10 μl of the coupling solution is added to the reaction container with care taken that the coupling and substrate solutions are well mixed. Because the Fast Blue BB salt solution is yellow it can easily be determined whether mixing is thorough. The color is then allowed to develop for 5 minutes. The Fast Blue BB salt reacts with oxaloacetate formed by the first reaction mixture to form a precipitate. The precipitate is blue but appears green within the solution because of the presence of the yellow coupling solution. The presence of greater amounts of oxaloacetate will result in increased amounts of precipitate and progressively deeper shades of green. observed to lower the color reaction threshold for detection of AST (i.e. a color signal is observed at a lower concentration of AST).

TABLE 1A pH = 8.0 (adjusted to 8.0 after adding substrates, if necessary)
15 MINUTE ASSAY

| Buffer Molarity | Color Rxn Time (Min) | B | 100 | 200 | AST Activity Sigma units/ml 500 | 1000 | 2000 | 4000 | 10000 |
|---|---|---|---|---|---|---|---|---|---|
| 0.01 | 5 | Y | Y | Y | Y | +1 | +2 | +3 | +5 |
|  | 10 | Y | Y | Y | Y or +½ | +1 | +2 | +4 | +6 |
| 0.02 | 5 | Y | Y | Y | +½ | +2 | +3 | +5 | +7 |
|  | 10 | YBr | YBr | +½ | +½ or 1 | +2 | +4 | +6 | +8 |
| 0.05 | 5 | YBr | YBr | YBr or +½ | +1 | +3 | +4 | +6 | +8 |
|  | 10 | YBr | YBr | YBr | +1 | +4 | +5 | +8 | +9 |
| 0.1 | 5 | YBr | YBr | +½ | +1 | +3 | +4 | +6 | +8 |
|  | 10 | Br | Br | Br | +1(Br) | +3 | +5 | +8 | +10 |

ABBREVIATIONS
Br = Brown; G = Green; O = Olive; Or = Orange; Y = Yellow
EXPLANATIONS
+½ = very pale green
+1 to +7 = darkness of green reaction product
+8 to +10 = very dark green to very dark blue

TABLE 1B

30 MINUTE ASSAY

| Buffer Molarity | Color Rxn Time (Min) | B | 100 | 200 | AST Activity Sigma Units/ml 500 | 1000 | 2000 | 4000 | 10000 |
|---|---|---|---|---|---|---|---|---|---|
| 0.01 | 5 | Y | Y | Y or +½ | +½ | +1 | +2 | +4 | +5 |
|  | 10 | Y | Y | YBr | +½ | +1 or 2 | +3 | +5 | +7 |
| 0.02 | 5 | Y | Y | +½ | +2 | +3 | +3 | +5 | +7 |
|  | 10 | Y | YBr | +½(YBr) | +2 | +4 | +4 | +6 | +9 |
| 0.05 | 5 | YBr | YBr | +1(GBr) | +3 | +4 | +5 | +7 | +10 |
|  | 10 | Br | Br | +1(GBr) | +3 | +4 | +6 | +8 | +10 |
| 0.1 | 5 | Y | Y or +½ | +1 | +2 | +4 | +5 | +8 | +10 |
|  | 10 | Br | Br | Br | +2(GBr) | +5 | +7 | +9 | +10 |

EXAMPLE 2

In this example, an assay of the enzyme AST was performed utilizing the method and materials of Example 1. Tris-HCl buffers were used at various molarities, and assays were conducted with 15 minute and 30 minute reaction times and 5 and 10 minute diazo dye coupling times. The pH of the enzyme reaction mixture was maintained at 8.0 The results shown in Tables 1A and 1 B indicate that the systems according to the invention are relatively insensitive to time either with respect to enzyme reaction time or color reaction time. This provides for flexibility in reading the test results and ensures that relatively minor operator errors in developing and reading the test will not affect the accuracy of the test. The results also reveal that the indicator threshold point, that point at which the color changes from yellow to green, may be altered by variation in the buffer molarity at a fixed pH. Increasing the buffer molarity under any set of reaction time conditions is

EXAMPLE 3

In this example, an assay of the enzyme AST was conducted utilizing the methods and materials of Example 1 at various buffer pH values. Table 2 shows the results of an assay with a 30 minute enzyme reaction time at four different pHs for varying amounts of AST for Fast Blue BB salt dissolved in buffer. Table 3 shows the results of assays conducted at four different pHs at 15 and 36 minute enzyme reaction times for various amounts of AST and Fast Blue BB salt dissolved in deionized water. It is apparent from the tables that higher enzyme reaction pH lowers the amount of AST required for color transition and hence lowers the AST detection threshold. It is also apparent by comparison of Table 2 with the 36 minute assay of Table 3 that the addition of buffer to the diazonium dyestuff tends to lower the AST detection threshold.

TABLE 2

30 MINUTE ASSAY

| Enzyme Rxn pH | Color Rxn pH | Color Rxn Time (Min) | B | 100 | 200 | AST Activity Sigma units/ml 500 | 1000 | 2000 | 4000 | 10000 |
|---|---|---|---|---|---|---|---|---|---|---|
| 7.0 | 6.75 | 5 | Y | Y | Y | +1 | +1 | +3 | +4 | +4 |
|  |  | 10 | Y | +½(YBr) | +½(YBr) | +1 | +2 | +3 | +5 | +6 |
| 7.4 | 7.05 | 5 | Y | +½ | +½ | +2 | +3 | +4 | +4 | +5 |
|  |  | 10 | YBr | +½ | +½ | +3 | +3 | +5 | +5 | +6 |
| 7.7 | 7.50 | 5 | Y | +1 | +1 | +1 | +3 | +5 | +5 | +6 |
|  |  | 10 | YBr | +1 | +1 | +1 | +3 | +6 | +8 | +10 |
| 8.0 | 7.86 | 5 | YBr | +½ | +2 | +4 | +4 | +4 | +6 | +9 |

TABLE 2-continued

30 MINUTE ASSAY

| Enzyme Rxn pH | Color Rxn pH | Color Rxn Time (Min) | B | 100 | 200 | AST Activity Sigma units/ml 500 | 1000 | 2000 | 4000 | 10000 |
|---|---|---|---|---|---|---|---|---|---|---|
| | | 10 | YBr | +½ | +2 | +4 | +4 | +5 | +8 | +10 |

TABLE 3

| Enzyme Rxn pH | Color Rxn pH | Color Rxn Time (Min) | B | 100 | 200 | 500 | 1000 | 2000 | 4000 | 10000 |
|---|---|---|---|---|---|---|---|---|---|---|
| | | | | 15 MINUTE ASSAY | | | | | | |
| 7.0 | 6.82 | 8 | Y | Y | Y | Y | +½ | +1 | +2 | +3 |
| 7.4 | 7.22 | 8 | Y | Y | Y | +½ | +1 | +2 | +4 | +6 |
| 7.7 | 7.54 | 8 | YBr | YBr | YBr | +1 | +2 | +4 | +5 | +8 |
| 8.0 | 7.86 | 8 | YBr | YBr | YBr | +1 | +3 | +5 | +8 | +10 |
| | | | | 36 MINUTE ASSAY | | | | | | |
| 7.0 | 6.82 | 5 | Y | Y | Y | +½ | +1 | +2 | +3 | +3 |
| | | 10 | Y | Y | Y | +½ | +1 | +3 | +4 | +4 |
| 7.4 | 7.22 | 5 | Y | Y | +½ | +1 | +3 | +4 | +5 | +7 |
| | | 10 | Y | Y | +½ | +2 | +4 | +5 | +6 | +8 |
| 7.7 | 7.54 | 5 | Y | Y | +½ | +2 | +3 | +6 | +8 | +9 |
| | | 10 | YBr | YBr | +1 | +3 | +4 | +7 | +8 | +10 |
| 8.0 | 7.86 | 5 | Y | +2 | +2 | +3 | +4 | +7 | +9 | +10 |
| | | 10 | YBr | +2 | +2 | +3 | +5 | +8 | +10 | +12 |

EXAMPLE 4

In this example, an assay of the enzyme AST was conducted utilizing the methods and materials of Example 1 at differing concentrations of the L-sodium aspartate and sodium alpha-ketoglutarate substrate solution as compared to that example. The assay was conducted at a pH of 8.0 with a 15 minute enzyme reaction time and 5 minute color reaction time. Table 4 shows that decreases in substrate concentration increases the AST detection threshold.

TABLE 4

15 MINUTE ASSAY
pH 8.0

| Substrate Conc. | Color Rxn Time (Min) | B | 100 | 200 | 500 | 1000 | 2000 | 4000 | 10000 |
|---|---|---|---|---|---|---|---|---|---|
| 2 × | 5 | Y | Y | +1 | +2 | +3 | +5 | +7 | +10 |
| 1 × | 5 | Y | Y | +1 | +2 | +3 | +5 | +7 | +10 |
| 0.5 × | 5 | Y | Y | +1 | +2 | +3 | +4 | +5 | +8 |
| 0.25 × | 5 | Y | Y | Y | +1 | +2 | +3 | +4 | +6 or 7 |
| 0.125 × | 5 | Y | Y | Y | +½ | +1 | +2 | +3 | +3 |
| 0.067 × | 5 | Y | Y | Y | Y | Y | +½ | +1 | +1 |

EXAMPLE 5

In this example, an assay of AST was performed utilizing the methods and materials of Example 1 while varying the concentration of Fast Blue BB salt used in the color reaction. Fast blue BB salt was used at a concentration of 10 mg per ml of deionized water (normal concentration) as well as at 5 mg per ml and 2 mg per ml. Ten µl of solution were added to the reaction mixture after 15 minutes of enzyme reaction time. The color reaction was allowed to proceed for either 5 or 10 minutes after addition of the Fast Blue BB salt. Table 5 demonstrates the effect of concentration of Fast Blue BB salt on the AST detection threshold. The results indicate that lower concentrations of the Fast Blue BB salt tend to raise the AST detection threshold.

TABLE 5

15 MINUTE ASSAY

| FBBB Conc. | Color Rxn Time (Min) | B | 100 | 200 | 500 | 1000 | 2000 | 4000 | 10000 |
|---|---|---|---|---|---|---|---|---|---|
| 2 mg | 5 | Y | Y | Y | Y | +1 | +2 | +3 | +4 |
| | 10 | Y | Y | Y | +½ | +1 or 2 | +2 | +3 or 4 | +5 |
| 5 mg | 5 | Y | +½ | +½ | +1 | +2 | +3 | +5 | +8 |
| | 10 | YBr | YBr | +½ | +1 or 2 | +3 | +4 | +6 | +10 |
| 10 mg | 5 | Y | +½ | +1 | +2 | +3 | +4 | +7 | +10 |
| | 10 | YBr | YBr | +½ | +2 | +4 | +5 | +9 | +10 |

EXAMPLE 6

In this example, an assay of AST was conducted utilizing the methods and materials of Example 1 with Fast Blue BB salt mixed with HCl at various normalities. The enzyme reaction was conducted for 30 minutes at a pH of 8.0 but pHs differed after addition of the Fast Blue BB salt/HCl solution mixture. The color reaction proceeded for 5 minutes. Table 6 demonstrates that lowering the concentration of HCl tended to decrease the AST detection threshold.

TABLE 6

30 MINUTE ASSAY
5 MINUTE COLOR REACTION TIME

| HCl Conc. | Enzyme Rxn pH | Color Rxn pH | B | 100 | 200 | 500 | 1000 | 2000 | 4000 | 10000 |
|---|---|---|---|---|---|---|---|---|---|---|
| 0.1 N | 8.0 | 7.18 | Y | Y | +½ | +1 | +2 | +2 | +5 | +6 |
| 0.067 N | 8.0 | 7.43 | Y | YBr | +1 | +2 | +2 | +3 | +5 | +8 |
| 0.05 N | 8.0 | 7.56 | Y | +½ | +½ | +2 | +3 | +5 | +8 | +10 |
| 0.04 N | 8.0 | 7.62 | Y | +½ | +1 | +2 | +3 | +6 | +8 | +10 |

EXAMPLE 7

In this example, an assay of AST was conducted utilizing the methods and materials of Example 1 wherein the effect of β-chloro-L-alanine added to the reaction mixture was determined. The enzyme reaction was conducted for 30 minutes at pH values of either 7.35 or 7.0 and the color reaction was allowed to proceed for either 5 or 10 minutes. Tables 7A and 7B demonstrate that addition of greater amounts of the inhibitor was observed to increase the AST detection threshold. The results indicate that lowering the reaction pH tends to increase the detection threshold. Differences in the color reaction time are not observed to significantly affect the assay results.

TABLE 7A

30 MINUTE ASSAY
pH 7.35

| CLA Conc. Molar | Color Rxn Time (Min) | B | 100 | 200 | 500 | 1000 | 2000 | 4000 | 10000 |
|---|---|---|---|---|---|---|---|---|---|
| None | 5 | Y | Y | Y | +1 | +2 | +3 | +4 | +6 |
|  | 10 | Y | Y | Y or +½ | +1 or 2 | +3 | +4 | +5 | +7 |
| 0.01 | 5 | Y | Y | Y or +½ | +1 | +1 or 2 | +3 | +4 | +6 |
|  | 10 | Y/YBr | Y/YBr | YBr or +½ | +1 | +2 | +3 | +4 | +7 |
| 0.05 | 5 | Y | Y | Y | Y or +½ | +1 | +2 | +4 | +5 |
|  | 10 | Y/YBr | Y/YBr | Y/YBr | +½ | +1 | +2 | +4 | +6 |
| 0.1 | 5 | Y | Y | Y | Y | +1(OG) | +2(OG) | +3(OG) | +4(OG) |
|  | 10 | YBr | YBr | YBr | YBr | +1(OG) | +2(OG) | +3(OG) | +4(OG) |

TABLE 7B

30 MINUTE ASSAY
pH 7.0

| CLA Conc. Molar | Color Rxn Time (Min) | B | 100 | 200 | 500 | 1000 | 2000 | 4000 | 10000 |
|---|---|---|---|---|---|---|---|---|---|
| None | 5 | Y | Y | Y | Y | +1 | +1 | +2 | +3 |
|  | 10 | Y | Y | Y | Y or +½ | +2 | +2 | +3 | +4 or 5 |
| 0.01 | 5 | Y | Y | Y | Y | +½ | +1 | +2 | +3 |
|  | 10 | Y | Y | Y | Y or +½ | +½ or 1 | +2 | +3 | +4 |
| 0.05 | 5 | Y | Y | Y | Y | Y | +½ | +1 | +1 |
|  | 10 | Y | Y | Y | Y | Y | +1 | +1 | +1 or 2 |
| 0.1 | 5 | Y | Y | Y | Y | Y | Y | +½ | +1 |
|  | 10 | Y | Y | Y | Y | Y | Y | +1 | +1 or 2 |

EXAMPLE 8

In this example, an assay of AST was conducted utilizing the methods and materials of Example 1 wherein the effect of addition of various amounts of the inhibitor d,l-c-propargylglycine was determined. The enzyme reaction was conducted for 30 minutes at pH values of either 7.35 or 7.0 and the color reaction was allowed to proceed for 5, 10 or 15 minutes. The results in tables 8A and 8B demonstrate that addition of greater amounts of the inhibitor tends to increase the AST detection threshold. In addition, higher concentrations of the inhibitor caused a less distinct transition from yellow to green at the detection threshold with intermediate orange-green and yellow-brown colors appearing between the yellow and green signals. Lower pH values were observed to raise the AST detection threshold and differences in color reaction times at higher pHs or higher concentrations of inhibitor were not observed to affect the assay results.

TABLE 8A

30 MINUTE ASSAY pH 7.4

| PAG Conc. Molar | Color Rxn Time (Min) | B | 100 | 200 | 500 | AST Activity Sigma units/ml 1000 | 2000 | 4000 | 10000 |
|---|---|---|---|---|---|---|---|---|---|
| None | 5 | Y | Y | +½ or 1 | +1 | +2 | +3 | +4 | +5 |
|  | 10 | Y | Y | +½ | +2 | +3 | +4 | +5 | +8 |
| 0.01 M | 5 | Y | Y | Y | +½ | +1 or 2 | +3 | +4 | +6 |
|  | 10 | YBr | YBr | YBr | +1 | +2 | +3 | +5 | +7 or 8 |
| 0.05 | 5 | Y | Y | Y | +½ | +1 | +2 | +3 | +4 |
|  | 10 | YBr | YBr | YBr | +½(YBr) | +2 | +3 | +3 | +5 |
|  |  |  |  |  |  | (OG 1000–10000, 5 & 10 minutes) | | | |
| 0.1 M | 5 | Y | Y |  | YBr | +1 | +1 | +2 | +3 |
|  | 10 | Or | Or |  | OrBr | +1 | +2 | +3 | +4 |
|  |  |  |  |  |  | (OG 1000–10000, 5 & 10 minutes) | | | |

TABLE 8B

30 MINUTE ASSAY pH 7.0

| PAG Conc. Molar | Color Rxn Time (Min) | B | 100 | 200 | 500 | 1000 | 2000 | 4000 | 10000 |
|---|---|---|---|---|---|---|---|---|---|
| None | 5 | Y | Y | Y | Y or +½ | +½ | +1 | +2 | +4 |
|  | 10 | Y | Y | +½ | +1 | +2 | +2 | +4 | +7 |
|  | 15 | Y | Y | +½ | +1 | +2 | +3 | +5 | +8 |
| 0.01 M | 5 | Y | Y | Y | Y | +1 | +1 | +2 | +4 |
|  | 10 | Y | Y | Y | +½ | +1 | +2 | +3 | +5 or 6 |
|  | 15 | Y | Y | Y | +½ | +1 | +3 | +4 | +7 |
| 0.05 M | 5 | Y | Y | Y | Y | Y | +1 | +2 | +3 |
|  | 10 | Y | Y | Y | Y | Y | +1 | +2 or 3 | +5 |
|  | 15 | YBr | YBr | YBr | YBr | YBr | +2 | +3 | +5 |
|  |  |  |  |  |  | (OG 2000–10000, 5–15 min) | | | |
| 0.1 M | 5 | Y | Y | Y | Y | Y | Y | +1(OG) | +(OG) |
|  | 10 | YBr | YBr | YBr | YBr | YBr | YBr | +1(OG) | +3(OG) |
|  | 15 | YBr | YBr | YBr | YBr | YBr | YBr | +2(OG) | +4(OG) |

As is illustrated by the preceding examples, it is well within the scope of the present invention to adjust the threshold point for detection of a specified level of AST. While it is generally contemplated that periodontal disease is indicated by the presence of AST in crevicular fluid at levels of from about 500 to about 4000 sigma units/ml or higher, the invention is not limited to detection thresholds of those specific AST concentrations. Indeed, through manipulation of substrate concentration, substrate incubation pH, the addition of specified concentrations of enzyme inhibitors and other modifications, it is possible to select virtually any detection threshold between about 100 and about 4000 sigma units/ml or higher.

Illustratively, Example 4 demonstrates that dramatic variation in reaction threshold that can be achieved by variation of substrate concentration. Similarly dramatic variations in reaction thresholds are illustrated in Examples 7 and 8 relating to the incorporation of varying amounts of enzyme inhibitors with the AST reaction mixture. Examples 2 and 3 illustrate the more subtle effects on threshold concentrations relating to incorporation of buffers at varying molarities and pH values.

In designing a system for detection of a reaction threshold at a particular concentration, it is contemplated that major adjustments in establishing a detection threshold may be brought about by modifying the substrate concentration and/or the type and concentration of enzyme inhibitors incorporated. Once such gross adjustments have been made to adjust a detection threshold, it is then contemplated that adjustments in buffer pH and molarity may be made to "fine tune" the reaction system to detect the presence of AST in excess of specific concentration thresholds.

What is claimed is:

1. In a method for detection of aspartate aminotransferase in an oral fluid sample through (1) incubation of the sample with aspartate aminotransferase substrates in a first reaction mixture to form a first reaction product and (2) detection of reaction product therein by incubation with an indicator substance in a second reaction mixture wherein a second, colored reaction product is formed, the improvement comprising:
   (a) utilizing a diazonium compound as the indicator substance in the second reaction mixture; and
   (b) modifying reaction conditions within the first and second reaction mixtures so that no visually detectable colored reaction product will be formed in the second reaction mixture when a selected subthreshold level of aspartate aminotransferase is present in said first reaction mixture but a visually detectable colored reaction product will be formed in the second reaction mixture when a selected nonzero suprathreshold concentration of aspartate aminotransferase is present in the first reaction mixture.

2. The improved method according to claim 1 wherein the oral fluid sample is crevicular fluid.

3. The improved method according to claim 1 wherein the oral fluid sample is saliva.

4. The improved method according to claim 1 wherein the aspartate aminotransferase substrates are aspartate and alpha-ketoglutarate and the first reaction product is oxaloacetate.

5. The improved method according to claim 1 wherein a modification of the first reaction mixture comprises adjusting the pH.

6. The improved method according to claim 1 wherein a modification of the first reaction mixture comprises adjusting the concentrations of aspartate and alpha-ketoglutarate.

7. The improved method according to claim 1 wherein a modification of the first reaction mixture comprises adjusting the buffer concentration.

8. The improved method according to claim 1 wherein a modification of the first reaction mixture comprises the addition of enzyme inhibitors.

9. The improved method according to claim 8 wherein the enzyme inhibitor is beta-chloro-L-alanine.

10. The improved method according to claim 8 wherein the enzyme inhibitor is d,l-c-propargylglycine.

11. The improved method according to claim 1 wherein a modification of the second reaction mixture comprises adjusting the buffer concentration.

12. The improved method according to claim 1 wherein a modification of the second reaction mixture comprises adjusting the pH.

13. The improved method according to claim 1 wherein a modification of the second reaction mixture comprises adjusting the indicator substance concentration.

14. The improved method according to claim 1 wherein the indicator substance is selected from the group consisting of Fast Violet B, Fast Red PDC/Ponceau L, Fast Red KL, Fast Scarlet GG, Fast Red RC, Fast Blue BB, Fast Blue B and FAst Blue RR.

15. The improved method according to claim 14 wherein the indicator substance is Fast Blue BB.

* * * * *

UNITED STATES PATENT AND TRADEMARK OFFICE
CERTIFICATE OF CORRECTION

PATENT NO. : 4,801,535

DATED : January 31, 1989

INVENTOR(S) : Babler et al.

It is certified that error appears in the above-identified patent and that said Letters Patent is hereby corrected as shown below:      Title page:

In the "OTHER PUBLICATIONS" section, change "Morin et al., Cun. Chem." to --Morin et al., Clin. Chem.--;

in the "Attorney, Agent or Firm" section, change "Marshall, O'Tolle," to --Marshall, O'Toole,--;

col. 1, line 52, change "sch" to --such--;

col. 4, lines 36-37, change "dinitrophenylhydrazone" to --dinitrophenylhydrazine--;

col. 4, lines 37-38, change "dinitrohydrazone" to --dinitrophenylhydrazine--;

col. 4, lines 41-61, "2,4-dinitrophenylhydrazine" should be joined with an arrow to the arrow joining "$CO_2$" and the structure of "pyruvate-2,4-dinitrophenylhydrazone"--;

col. 5, line 40, before "2.5" insert --{--;

col. 5, line 40, change "]" to --}--;

UNITED STATES PATENT AND TRADEMARK OFFICE
CERTIFICATE OF CORRECTION

PATENT NO. : 4,801,535

DATED : January 31, 1989

INVENTOR(S) : Babler et al.

It is certified that error appears in the above-identified patent and that said Letters Patent is hereby corrected as shown below:

col. 6, line 44, omit the comma after "acid";

col. 7, line 5, change "with" to --which--;

col. 8, line 3, change "dye stuff" to --dyestuff--;

col. 9, line 16, change "0.M" to --0.1M--;

col. 10, line 14, between "par" and "icular" insert --t--;

col. 17, Table 8A, under 500 column, change "+1/2(YBr)" to --YBr or +1/2--;

col. 17, Table 8B, under 10000 column, change "+(OG)" to --+3(OG)--.

Signed and Sealed this

Twenty-third Day of January, 1990

*Attest:*

JEFFREY M. SAMUELS

*Attesting Officer*   *Acting Commissioner of Patents and Trademarks*